United States Patent
Herceg et al.

(10) Patent No.: US 12,138,031 B2
(45) Date of Patent: Nov. 12, 2024

(54) APPARATUS, ELECTRONIC DEVICE AND METHOD FOR ESTIMATING IMPEDANCE

(71) Applicant: Nokia Technologies Oy, Espoo (FI)

(72) Inventors: Marijan Herceg, Osijek (HR); Tomislav Matic, Osijek (HR)

(73) Assignee: Nokia Technologies Oy, Espoo (FI)

( * ) Notice: Subject to any disclaimer, the term of this patent is extended or adjusted under 35 U.S.C. 154(b) by 1077 days.

(21) Appl. No.: 17/044,876

(22) PCT Filed: Apr. 11, 2019

(86) PCT No.: PCT/EP2019/059209
§ 371 (c)(1),
(2) Date: Oct. 2, 2020

(87) PCT Pub. No.: WO2019/197517
PCT Pub. Date: Oct. 17, 2019

(65) Prior Publication Data
US 2021/0100473 A1    Apr. 8, 2021

(30) Foreign Application Priority Data
Apr. 13, 2018 (EP) ..................... 18167365

(51) Int. Cl.
*A61B 5/053* (2021.01)
*A61B 5/00* (2006.01)

(52) U.S. Cl.
CPC .......... *A61B 5/053* (2013.01); *A61B 5/6823* (2013.01); *A61B 5/6831* (2013.01)

(58) Field of Classification Search
CPC ..... A61B 5/053; A61B 5/0531; A61B 5/6823; A61B 5/6831; G01R 27/02; G01N 27/228
See application file for complete search history.

(56) References Cited

U.S. PATENT DOCUMENTS 5,678,547 A    10/1997  Faupel et al.
6,633,777 B2   10/2003  Szopinski
(Continued)

FOREIGN PATENT DOCUMENTS

DE    4420998 A1    12/1995
DE    10028671 A1   10/2001
(Continued)

OTHER PUBLICATIONS

"Bodystat-Body Composition Technology", Bodystat, Retrieved on Sep. 23, 2020, Webpage available at : https://www.bodystat.com/.
(Continued)

*Primary Examiner* — Devin B Henson
(74) *Attorney, Agent, or Firm* — Harrington & Smith (57) ABSTRACT

The application relates to an apparatus, electronic device and method. The apparatus comprises circuitry configured to provide a direct current signal to a subject. The circuitry is configured to enable switching between a first circuit loop and a second circuit loop. The first circuit loop is configured to enable charging of a capacitor to enable measurement of a first time constant to be obtained where the first time constant is indicative of a charging time of the capacitor. The second circuit loop is configured to enable discharging of the capacitor to enable measurement of a second time constant to be obtained where the second time constant is indicative of a discharging time of the capacitor. The first time constant and the second time constant enable an impedance of the subject to be estimated.

19 Claims, 4 Drawing Sheets

(56) References Cited

U.S. PATENT DOCUMENTS

| | | | |
|---|---|---|---|
| 6,724,200 B2 | 4/2004 | Fukuda | |
| 6,725,091 B2 | 4/2004 | Dal Molin | |
| 7,006,078 B2 | 2/2006 | Kim | |
| 9,770,185 B2 * | 9/2017 | Wheeler | A61B 5/0533 |
| 2004/0075446 A1 | 4/2004 | Haas et al. | |
| 2005/0113712 A1 | 5/2005 | Petrucelli | |
| 2006/0267599 A1 | 11/2006 | Pooranakaran et al. | |
| 2013/0249575 A1 | 9/2013 | Hertes | |
| 2014/0159747 A1 | 6/2014 | Frantz | |
| 2017/0049352 A1 * | 2/2017 | Mirov | A61B 5/0533 |

FOREIGN PATENT DOCUMENTS

| | | | |
|---|---|---|---|
| DE | 102008042765 A1 | 4/2010 | |
| EP | 1584290 A1 | 10/2005 | |
| JP | 3621586 B2 | 2/2005 | |
| JP | 2005342376 A | 12/2005 | |
| WO | 2011/074683 A1 | 6/2011 | |

OTHER PUBLICATIONS

"Your Partner in Innovative Diagnostic Technology", SMT medical, Retrieved on Sep. 23, 2020, Webpage available at : https://www.smt-medical.com/en/home.html.

Yang et al., "Impedance Measurement with the AFE4300", Texas Instruments, Application Report SBAA202, Oct. 2013, 13 pages.

Conchell, "Bio-Impedance Circuit Design for Body Worn Systems", Analog Devices, Aug. 7, 2014, pp. 1-10.

"Ultra-Low-Power, Single-Channel Integrated Biopotential (ECG, R-to-R, and Pace Detection) and Bioimpedance (BioZ) AFE", Maxim Integrated, MAX30001, Aug. 2019, pp. 1-87.

Yang et al., "A Portable Human Skin Tester Based on Resistance and Capacitance Measurement", Advanced Materials Research vol. 1035, 2014, pp. 401-407.

Abad, "Development of a Capacitive Bioimpedance Measurement System", Thesis, Aug. 24, 2009, 109 pages.

"Ultra-Low Power, Single-Channel Integrated Biopotential (ECG, R to R Detection) AFE", Maxim Integrated, MAX30003, Sep. 2019, pp. 1-46.

"Ultra-Low Power, Single-Channel Integrated Biopotential (R-to-R Detection) AFE", Maxim Integrated, MAX30004, Dec. 2016, pp. 1-39.

Extended European Search Report received for corresponding European Patent Application No. 18167365.8, dated Nov. 28, 2018, 7 pages.

International Search Report and Written Opinion received for corresponding Patent Cooperation Treaty Application No. PCT/EP2019/059209, dated Jul. 12, 2019, 11 pages.

* cited by examiner

APPARATUS, ELECTRONIC DEVICE AND METHOD FOR ESTIMATING IMPEDANCE

RELATED APPLICATION

This application claims priority to PCT Application No. PCT/EP2019/059209, filed on Apr. 11, 2019, which claims priority to EP application Ser. No. 18/167,365.8, filed on Apr. 13, 2018 each of which is incorporated herein by reference in its entirety.

TECHNOLOGICAL FIELD

Examples of the present disclosure relate to an apparatus, electronic device and method for estimating impedance. Some examples relate to an apparatus, electronic device and method for estimating impedance of a subject.

BACKGROUND

The impedance of a subject can be used for monitoring purposes. For example it can be used for monitoring blood vessel diameter, measuring body composition, stress level prediction or other suitable purposes.

BRIEF SUMMARY

According to various, but not necessarily all, examples there is provided an apparatus comprising: circuitry configured to provide a direct current signal to a subject; wherein the circuitry is configured to enable switching between a first circuit loop and a second circuit loop and the first circuit loop is configured to enable charging of a capacitor to enable measurement of a first time constant to be obtained where the first time constant is indicative of a charging time of the capacitor and the second circuit loop is configured to enable discharging of the capacitor to enable measurement of a second time constant to be obtained where the second time constant is indicative of a discharging time of the capacitor; and wherein the first time constant and the second time constant enable an impedance of the subject to be estimated.

The circuitry may be configured so that when the apparatus is in use the capacitor is in series with the subject.

The first circuit loop may comprise a power source.

The first circuit loop may comprise a first resistor in series with the capacitor and the second circuit loop comprises a second resistor in series with the capacitor.

The first resistor may have a different resistance to the second resistor.

The apparatus may comprise compensation circuitry configured to detect a change in impedance at an interface between the circuitry and the subject and, in response to the detected change, adjust the resistance of the first resistor and/or the second resistor.

The apparatus may comprise one or more switches configured to close the first circuit loop and open the second circuit loop for a first time period and close the second circuit loop and open the first circuit loop for the second time period wherein the first time period is different to the second time period.

The apparatus may comprise control circuitry configured to cause a first switch to be opened and a second switch to be closed in response to a threshold voltage level being reached. The control circuitry may be configured to provide output pulses wherein the duration of the output pulses provides an indication of the first time constant and/or the second time constant. The apparatus may comprise processing circuitry configured to estimate an impedance of the subject from the output pulses of the control circuitry. The control circuitry may comprise at least one of a Schmitt trigger, a window comparator, which is configured to control the position of the switches based on a threshold voltage being reached. The impedance of the subject may be estimated using look up tables.

The apparatus may comprise at least a first electrode and at least a second electrode are configured to provide an interface between the circuitry and the subject.

According to various, but not necessarily all, examples there is provided an electronic device comprising an apparatus as claimed in any preceding claim.

According to various, but not necessarily all, examples there is provided a method comprising: configuring circuitry to provide a direct current signal to a subject; configuring the circuitry to enable charging of a capacitor through a first current loop so as to enable measurement of a first time constant to be obtained where the first time constant is indicative of a charging time of the capacitor; and configuring the circuitry to enable discharging of the capacitor through a second current loop so as to enable measurement of a second time constant to be obtained where the second time constant is indicative of a discharging time of the capacitor; wherein the first time constant and the second time constant enable an impedance of the subject to be estimated.

BRIEF DESCRIPTION

Some example embodiments will now be described with reference to the accompanying drawings in which.

DETAILED DESCRIPTION

The Figures illustrate an apparatus 101, electronic device 401 and method. The apparatus 101 comprises circuitry 103 configured to provide a direct current signal to a subject 105. The circuitry 103 is configured to enable switching between a first circuit loop 107 and a second circuit loop 109. The first circuit loop 107 is configured to enable charging of a capacitor 111 to enable measurement of a first time constant $T_1$ to be obtained where the first time constant $T_1$ is indicative of a charging time of the capacitor 111. The second circuit loop 109 is configured to enable discharging of the capacitor 111 to enable measurement of a second time constant $T_2$ to be obtained where the second time constant $T_2$ is indicative of a discharging time of the capacitor 111. The first time constant $T_1$ and the second time constant $T_2$ enable an impedance of the subject 105 to be estimated.

Examples of the disclosure therefore provide for an apparatus 101 which can estimate the impedance of a subject 105 using a direct current signal. This may reduce the power needed and the complexity of the apparatus 101 and circuitry 103 within the apparatus 101 compared to an apparatus which uses an alternating current signal. The apparatus 101 could be used in electronic devices 401 such as wearable electronic devices.

Figure 1:
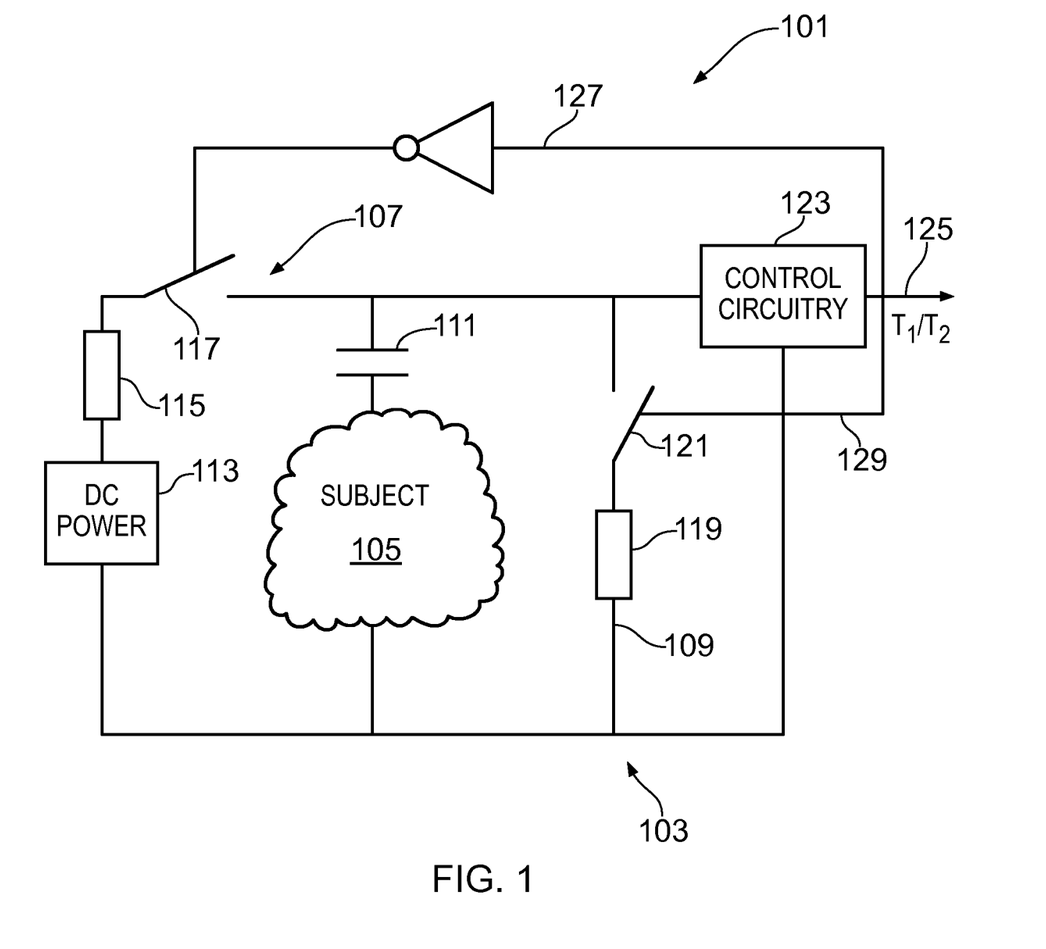
FIG. 1 shows an example embodiment of the subject matter described herein.

FIG. 1 illustrates an example apparatus 101. The apparatus 101 comprises circuitry 103 which is configured to provide a direct current signal to a subject 105.

The subject 105 could be a human or other suitable subject, such as an animal. In some examples the subject 105 could be wearing the apparatus 101 within a wearable electronic device. The impedance of the subject 105 can be represented as a capacitance in parallel with a resistance. As the impedance of the subject 105 comprises two components, two measurements need to be made by the circuitry 103 in order to enable the two components of the impedance of the subject 105 to be estimated.

In the example of FIG. 1 the circuitry 103 comprises a first circuit loop 107, a second circuit loop 109 and control circuitry 123.

The circuit loops 107, 109 comprise sections of the circuitry 103 which can be closed by the closing of respective switches 117, 121 and by coupling the circuitry 103 to the subject 105.

The first circuit loop 107 is configured to enable charging of a capacitor 111. The first circuit loop 107 is configured to enable charging of the capacitor 111 when the circuitry 103 is coupled to a subject 105.

In the example circuitry 103 of FIG. 1 the first circuit loop 107 comprises a power source 113, a first resistor 115, a first switch 117 and the capacitor 111.

The first circuit loop 107 of the circuitry 103 is configured so that, when the apparatus 101 is in use with the circuitry 103 coupled to a subject 105, the capacitor 111 is in series with the subject 105. The first circuit loop 107 is configured to enable a measurement of a first time constant $T_1$ to be obtained. The first time constant $T_1$ is indicative of a charging time of the capacitor 111.

A power source 113 is also provided within the first circuit loop 107. The power source 113 comprises a direct current power source. The power source 113 could comprise a battery or any other suitable type of power source.

The first resistor 115 is also provided within the first circuit loop 107. The first resistor 115 is configured within the first circuit loop 107 so that the charging time for the capacitor 111 is dependent upon the resistance of the first resistor 115. In the example of FIG. 1 the first resistor 115 is positioned within the first circuit loop 107 so that when the first switch 117 is closed the first resistor 115 is in series with the first capacitor 111 and the subject 105.

The first switch 117 comprises any means suitable for opening and closing the first circuit loop 107. The first switch 117 is configured so that when the apparatus 101 is in use with the circuitry 103 coupled to a subject 105 closing the first switch 117 completes the first circuit loop 107 and enables charging of the capacitor 111.

The first switch 117 is coupled to the control circuitry 123. The first switch 117 is coupled to the control circuitry 123 so that a first control signal 127 can be provided from the control circuitry 123 to the first switch 117. This may enable the control circuitry 123 to control when the first switch 117 is opened and closed. In some examples the control circuitry 123 may be configured to cause the first switch 117 to be opened once a threshold level has been reached for the voltage on the capacitor 111. The threshold voltage level could be any predetermined voltage level between zero and the voltage level of the power source 113. In some examples the threshold voltage level could be the maximum voltage level, or substantially the maximum voltage level. The maximum voltage level could be the voltage level of the power source 113.

In the example circuitry 103 of FIG. 1 the second circuit loop 109 comprises a second resistor 119, a second switch 121 and the capacitor 111. In the example of FIG. 1 the second circuit loop 109 comprises some of the same sections of circuitry as the first circuit loop 107. In the example of FIG. 1 both the first circuit loop 107 and the second circuit loop 109 comprise the capacitor 111 and both the first circuit loop 107 and the second circuit loop 109 can be coupled to the subject 105. The second circuit loop 109 also comprises some sections of the circuitry which are not provided within the first circuit loop 107. For example, the second resistor 119 and the second switch 121 are positioned within the second circuit loop 109 but not the first circuit loop 107. Also the second circuit loop 109 does not contain some sections of circuitry which are positioned within the first circuit loop 107. For example, the power source 113 and the first resistor 115 are provided within the first circuit loop 107 but not the second circuit loop 109.

The second circuit loop 109 of the circuitry 103 is configured so that, when the apparatus 101 is in use, with the circuitry 103 coupled to a subject 105, the capacitor 111 is in series with the subject 105. The second circuit loop 109 is configured to enable a measurement of a second time constant $T_2$ to be obtained. The second time constant $T_2$ is indicative of a discharging time of the capacitor 111.

The second resistor 119 is configured within the second circuit loop 109 so that the discharging time for the capacitor 111 is dependent upon the resistance of the second resistor 119. In the example of FIG. 1 the second resistor 119 is positioned within the second circuit loop 109 so that when the second switch 121 is closed the second resistor 119 is in series with the capacitor 111 and the subject 105.

The second resistor 119 may have a different resistance to the first resistor 115. The difference in the resistances of the first resistor 115 and the second resistor 119 may ensure that the first time constant $T_1$ has a different value to the second time constant $T_2$. The difference in the resistances of the first resistor 115 and the second resistor 119 may ensure that the time taken for charging of the capacitor 111 is different to the time taken to discharge the capacitor 111.

The second switch 121 comprises any means suitable for opening and closing the second circuit loop 109. The second switch 121 is configured so that when the apparatus 101 is in use with the circuitry 103 coupled to a subject 105 closing the second switch 121 completes the second circuit loop 109 and enables discharging of the capacitor 111.

The second switch 121 is coupled to the control circuitry 123. The second switch is coupled to the control circuitry so that the control circuitry 123 can provide a control second control signal 129 to the second switch 121. This may enable the control circuitry 123 to control when the second switch 121 is opened and closed. In some examples the control circuitry 123 may be configured to cause the second switch 121 to be closed once a threshold level has been reached for the voltage of the capacitor 111. The threshold voltage level could be any predetermined voltage level between zero and the voltage level of the power source 113. In some examples the threshold voltage level could be the maximum voltage level, or substantially the maximum voltage level. The maximum voltage level could be the voltage level of the power source 113.

The control circuitry 123 may control both the first switch 117 and the second switch 121. The control circuitry 123 may control the switches 117, 121 so that when the first switch 117 is open the second switch 121 is closed. The control circuitry 123 may control the switches 117, 121 so that when the first switch 117 is closed the second switch 121 is open.

The control circuitry 123 may comprise any means which may be configured to provide a control signal to one or both of the switches 117, 121 in response to a threshold voltage being reached on the capacitor 111. The control circuitry 123 may comprise a Schmitt trigger, a window comparator or any other suitable means.

The control circuitry 123 may also be configured to provide an output signal 125 where the output signal 125 comprises information indicative of the first time constant $T_1$ and the second time constant $T_2$. In some examples the output signal 125 may comprise pulses where the duration of the pulses provides an indication of the first time constant $T_1$ and/or the second time constant $T_2$.

The circuitry 103 may be configured so that the output signal 125 from the control circuitry 123 can be provided to processing circuitry to enable the time constants $T_1$, $T_2$ to be estimated. In some examples the processing circuitry may be provided within the same apparatus 101 as the circuitry 103 so that the output signal 125 can be provided directly from the circuitry 103 to the processing circuitry. In other examples the processing circuitry could be provided in a separate apparatus. In such cases the output signal 125 may be provided to transceiver circuitry to enable the output signal 125 to be transmitted to the processing circuitry.

Figure 2A:
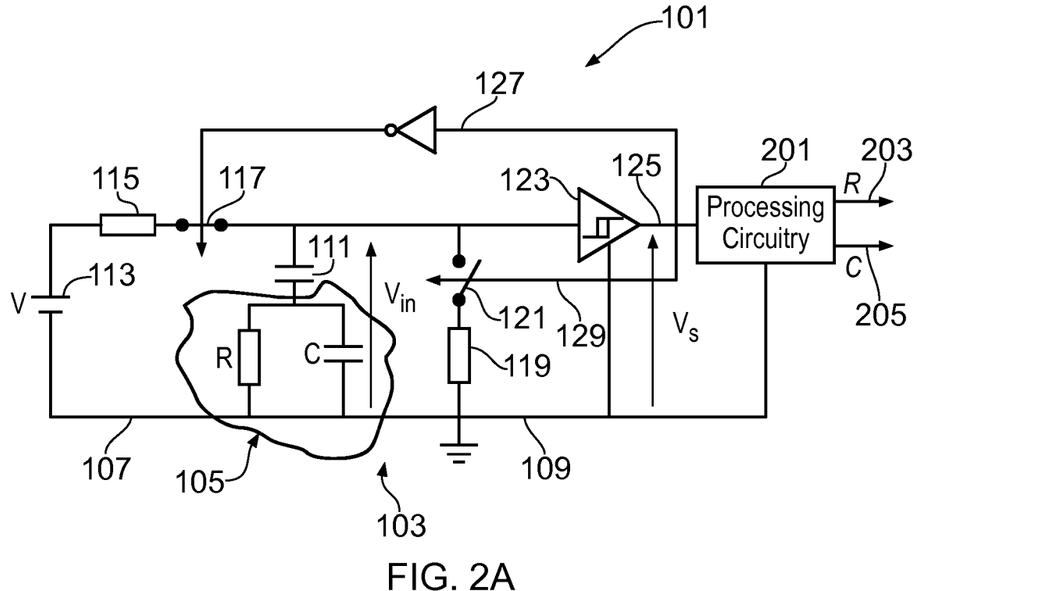
FIGS. 2A to 2C show another example embodiment of the subject matter described herein.

FIG. 2A shows another example apparatus 101 according to examples of the disclosure. The apparatus 101 comprises circuitry 103 comprising a first circuit loop 107 and a second circuit loop 109. The first circuit loop 107 and the second circuit loop 109 may be as shown in FIG. 1. Corresponding reference numerals are used for corresponding features.

In the example of FIG. 2A the control circuitry 123 comprises a Schmitt trigger 205. Other types of control circuitry 123 may be used in other examples of the disclosure. For example a window comparator, or any other suitable means could be used.

In the example of FIG. 2A the apparatus 101 also comprises processing circuitry 201. The processing circuitry 201 is coupled to the control circuitry 123 so that the output signal 125 from the control circuitry 123 is provided to the processing circuitry 201.

The processing circuitry 201 comprises any means which may be configured to process the output signal 125 from the control circuitry 123 so as to provide one or more output signals indicative of the impedance of the subject 105. In the example of FIG. 2A the processing circuitry 201 is configured to provide a first output signal 203 indicative of the resistance of the subject 105 and a second output signal 205 indicative of the capacitance of the subject 105.

In some examples the resistance of the subject 105 and the capacitance of the subject 105 may be estimated by using look up tables. The look up tables may be stored in memory circuitry which may be accessed by the processing circuitry 201. Other methods for estimating the resistance of the subject 105 and the capacitance of the subject 105 could be used in other examples of the disclosure.

In the example of FIG. 2A the resistance of the subject 105 and the capacitance of the subject 105 may be estimated from the time constants $T_1$ and $T_2$. The time constants $T_1$ and $T_2$ may be derived from the duration of pulses within the output signal 125 from the control circuitry 123. The value of the time constants $T_1$ and $T_2$ are dependent upon the impedance of the subject 105 so that the duration of the pulses gives a measure of the impedance of the subject 105.

Other methods of determining the resistance of the subject 105 and the capacitance of the subject 105 may be used in other examples of the disclosure. For instance, in some examples a fitting function could be used to estimate the resistance and the capacitance from the time constants $T_1$ and $T_2$. The fitting function could be obtained empirically. In some examples the resistance and the capacitance could be estimated from analytical expressions which could be obtained by solving circuit transient equations. Therefore the resistance and the capacitance of the subject 105 may be estimated from the duration of pulses in an output signal 125 using any suitable process.

Figure 2B:
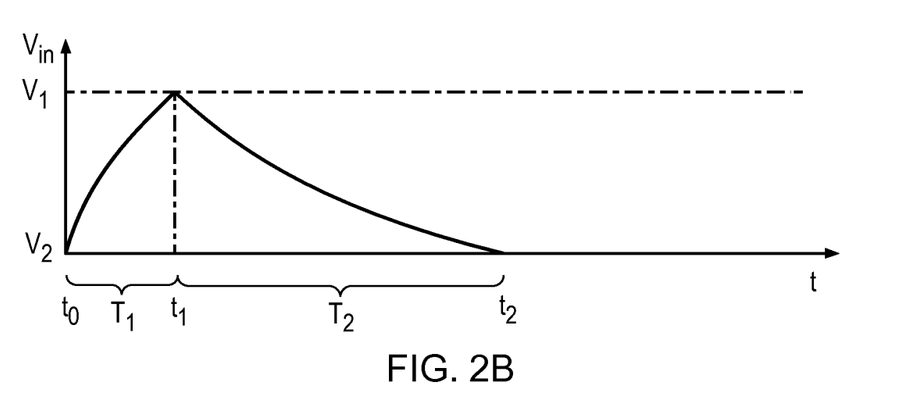

FIG. 2B shows a plot of the voltage $V_{in}$ of the capacitor 111 during a charging and discharging cycle for the apparatus 101 shown in FIG. 2A. At time to the first switch 117 is closed and the second switch 121 is opened. This enables charging of the capacitor 111 through the first circuit loop 107.

At time $t_1$ a threshold voltage $V_1$ is reached. The threshold voltage $V_1$ may be any predetermined voltage level between sero and the voltage level of the power source 113. In some examples the threshold voltage $V_1$ may be the fully charged voltage of the capacitor 111 or the voltage of the capacitor 111 when it is substantially fully charged. The fully charged maximum voltage level could be the voltage level of the power source 113.

The time taken to reach the threshold voltage $V_1$ may be indicative of the time constant $T_1$. The time constant $T_1$ is dependent upon the resistance of the first resistor 115 and the impedance of the subject 105.

Once the threshold voltage $V_1$ has been reached the control circuitry 123 provides a first control signal 127 to open the first switch 117 and a second control signal 129 to close the second switch 121. This breaks the first circuit loop 107 and completes the second circuit loop 109. This enables the capacitor 111 to be discharged through the second circuit loop 109. The capacitor 111 is discharged until a lower threshold voltage $V_2$ is reached. In the example of FIG. 2B the lower threshold voltage $V_2$ is zero, or substantially zero.

At time $t_2$ the lower threshold voltage $V_2$ is reached. The time taken to reach the lower threshold voltage $V_2$ may be indicative of the time constant $T_2$. The time constant $T_2$ is dependent upon the resistance of the second resistor 119 and the impedance of the subject 105.

As the first resistor 115 and the second resistor 119 have different values the first time constant $T_1$ and the second time constant $T_2$ also have different values.

Figure 2C:
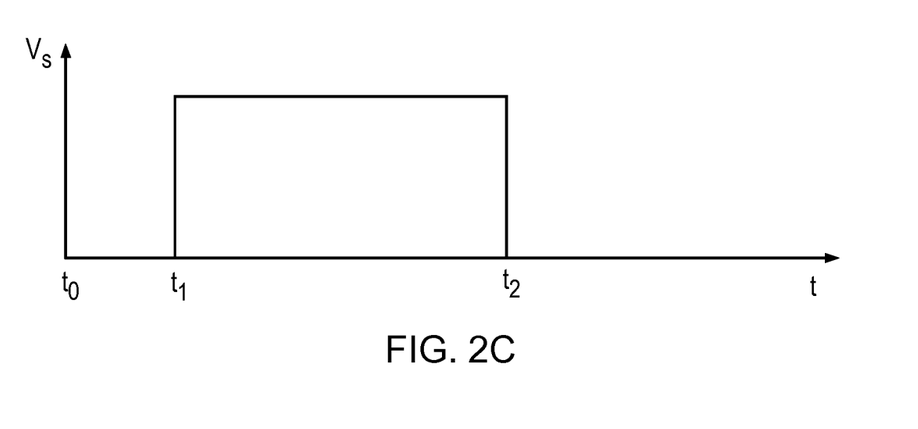

FIG. 2C shows a plot of the output signal 125 provided by the control circuitry 123 during the charging and discharging cycle. Between time $t_0$ and $t_1$ the voltage of the capacitor 111 is below the threshold voltage $V_1$ and so the voltage $V_s$ of the control circuitry 123 is zero, or substantially zero, during this time period. Once the threshold voltage $V_1$ is reached, at time $t_1$ then the voltage $V_s$ of the output signal 125 is increased to a non-zero value. Between time $t_1$ and $t_2$ the voltage of the capacitor 111 is above the lower threshold voltage $V_2$ and so the voltage $V_s$ of the output signal 125 remains at the non-zero value during this time period. In the example of FIGS. 2A to 2C the output of the control circuitry 123 remains at a constant value, or a substantially constant value, during this time period. Once the capacitor 111 has been discharged so that the lower threshold voltage $V_2$ is reached, at time $t_2$ then the voltage $V_s$ of the output signal 125 is decreased back to the original value, which in this case is zero, or substantially zero.

Therefore the output signal 125 of the control circuit 123 is a series of pulses where the duration of the pulses is indicative of the time constants $T_1$ and $T_2$. The values of the capacitance and the resistance of the subject 105 can be estimated from the duration of the pulses so as to provide the first output signal 203 and the second output signal 205.

Figure 3A:
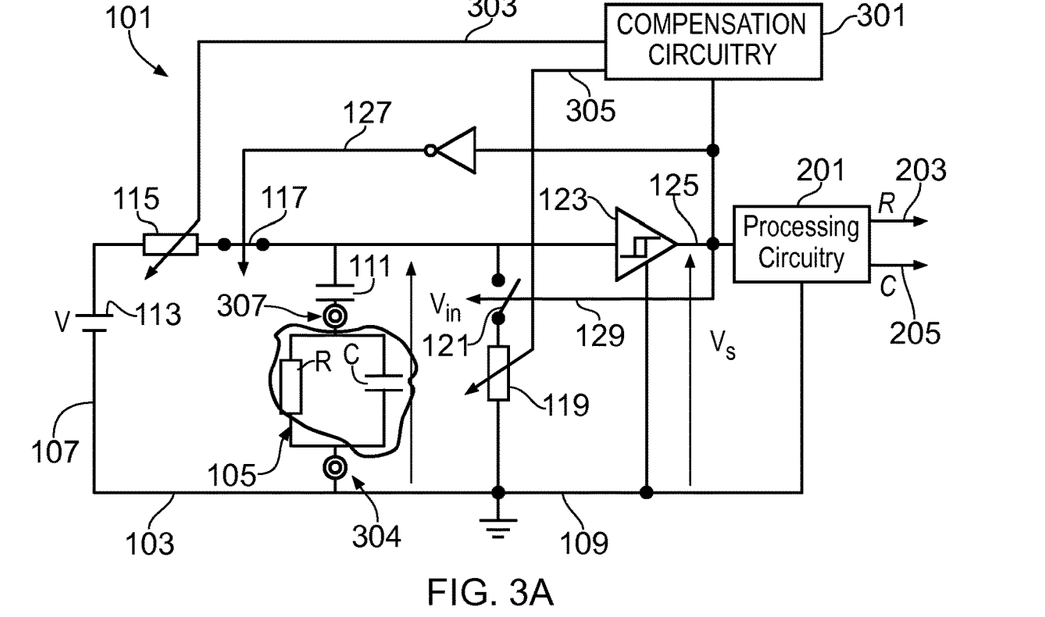
FIGS. 3A to 3C show another example embodiment of the subject matter described herein.

FIG. 3A shows another example apparatus 101 according to examples of the disclosure. The apparatus 101 comprises circuitry 103 comprising a first circuit loop 107, a second circuit loop 109 and processing circuitry 201. The first circuit loop 107, the second circuit loop 109 and the processing circuitry 201 may be as shown in 2A. Corresponding reference numerals are used for corresponding features.

In the example of FIG. 3A the circuitry 103 comprises a first electrode 307 and a second electrode 309. The first electrode 307 and the second electrode 309 provide an interface between the subject 105 and the circuitry 103. The first electrode 307 and the second electrode 309 may comprise any suitable means which may enable the direct current signal from the circuitry 103 to be provided to the subject 105. The circuitry 103 is configured so that when the circuitry 103 is in use the electrodes 307, 309 may be provided in direct contact to the skin of the subject 105. In some examples the electrodes 307, 309 could comprise adhesive electrodes which may be adhered to the skin of the subject 105. Other types of electrode 307, 309 could be used in other examples of the disclosure.

In addition to the first circuit loop 107, the second circuit loop 109 and the processing circuitry 201 the apparatus 101 also comprises compensation circuitry 301. The compensation circuitry 301 may comprise any means which may be configured to detect a change in impedance at an interface between the circuitry 103 and the subject 105 and, in response to the detected change, adjust the resistance of the first resistor 115 and/or the second resistor 119. The change in the impedance at the interface could be caused by movement of the electrodes 307, 309, by dirt or moisture accumulating around the electrode 307 or by any other suitable factor.

The compensation circuitry 301 is coupled to the control circuitry 123 so that an output signal 125 of the control circuitry 123 is provided to the compensation circuitry 301. This enables the compensation circuitry 301 to use the output signal 125 to determine if there has been a change in the impedance at an interface between the circuitry 103 and the subject 105.

In the example of FIG. 3A the compensation circuitry 301 is coupled to the first resistor 115 so that a first compensation signal 303 is provided from the compensation circuitry 301 to the first resistor 115. The first resistor 115 comprises a variable resistor and the first compensation signal 303 causes the resistance of the variable resistor to be controlled. The first compensation signal 303 may cause the resistance of the variable resistor to be increased, decreased or stay the same as is determined by the compensation circuitry 301.

The compensation circuitry 301 is also coupled to the second resistor 119 so that a second compensation signal 305 is provided from the compensation circuitry 301 to the second resistor 119. The second resistor 119 comprises a variable resistor and the second compensation signal 305 causes the resistance of the variable resistor to be controlled. The second compensation signal 305 may cause the resistance of the variable resistor to be increased, decreased or stay the same as is determined by the compensation circuitry 301.

In the example of FIG. 3A the compensation circuitry 301 is configured to compensate for a change of the impedance at the interface between the subject 105 and the circuitry 103. The compensation circuitry 301 may be configured to compensate for a change of the impedance which is above a threshold value. The changes in impedance at the interface between the subject 105 and the circuitry 103 may be significantly larger than changes in impedance caused by biometric parameters. This may enable small changes in impedance to be discounted by the compensation circuitry 301. In such examples it is not necessary for the absolute value of the impedance at the interface between the subject 105 and the circuitry 103 to be determined.

Figure 3B:
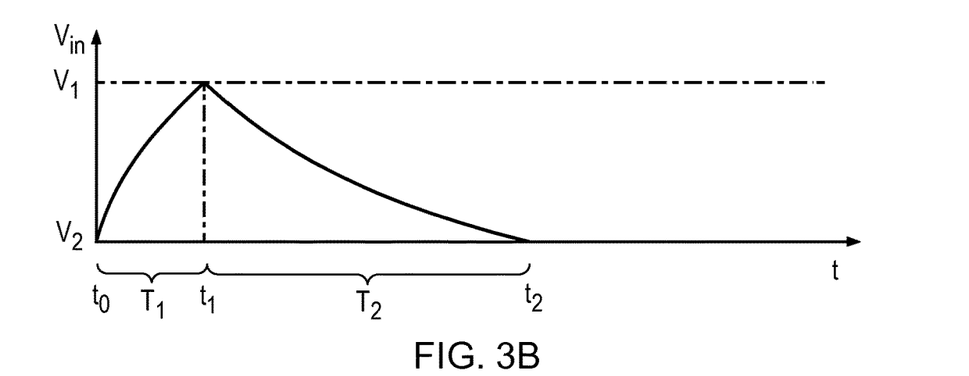
Figure 3C:
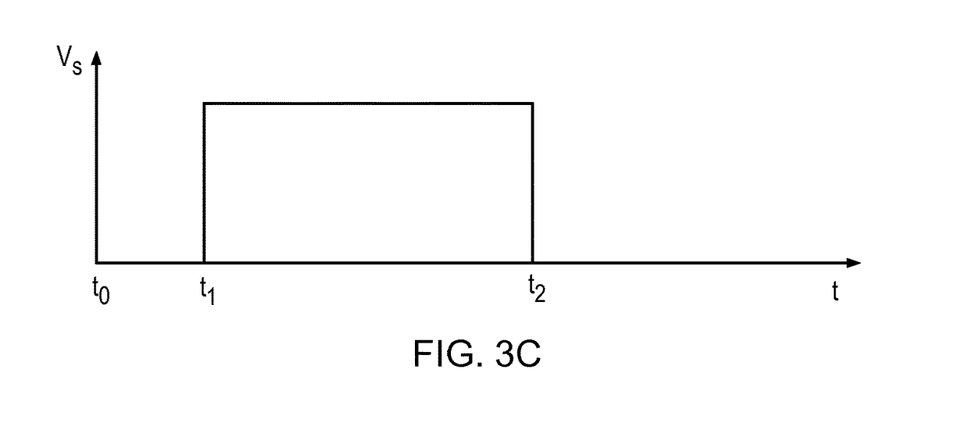

FIG. 3B shows a plot of the voltage $V_{in}$ of the capacitor 111 during a charging and discharging cycle for the apparatus 101 shown in FIG. 3A and FIG. 3C shows a plot of the voltage $V_s$ of the output signal 125 provided by the control circuitry 123 during the charging and discharging cycle. These plots are similar to those shown in FIGS. 2A and 2B.

Figure 4:
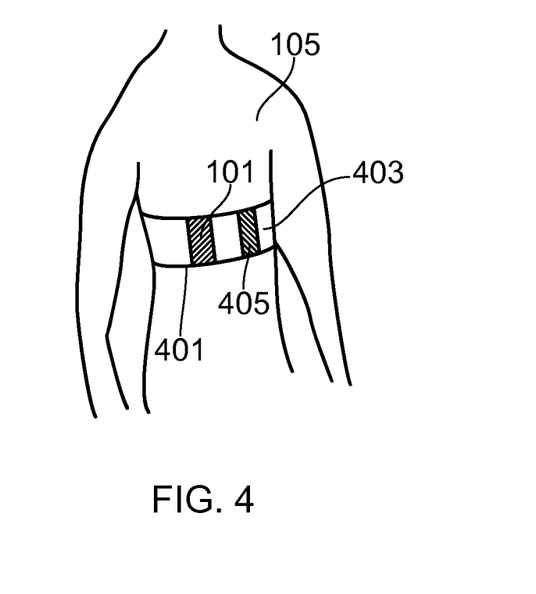
FIG. 4 shows an example embodiment of an electronic device.

FIG. 4 shows an example embodiment of an electronic device 401 which may comprise an apparatus 101 such as the apparatus 101 described above.

In the example of FIG. 4 the electronic device 401 comprises a wearable device. In the example of FIG. 4 the electronic device 401 is provided on a chest strap 403 which enables the apparatus 101 to be positioned adjacent to the torso of the subject 105. The chest strap 403 may provide attachment means which enable the electronic device 401 to be attached to the subject 105. In other examples the apparatus 101 could be positioned adjacent to other parts of the subject 105 such as an arm or a leg or any other suitable part. In such examples other types of attachment means may be provided instead of a chest strap.

In the example of FIG. 4 the electronic device 401 may also comprise one or more transceivers 405. The one or more transceivers 405 could be configured to enable data to be transmitted between the electronic device 401 and another device. The another device could be a mobile phone, a communications device or any other suitable type of device. The another device could comprise processing circuitry 201 which may be configured to estimate the impedance of the subject 105 from the output signal 125 of the electronic device 401.

In some but not necessarily all examples, the electronic device 401 may be configured to communicate data from the electronic device 401 with or without local storage of the data in a memory provided within the electronic device 401 and with or without local processing of the data by circuitry or processors within the electronic device 401.

The data may, for example, be measurement data from the circuitry 103. For example the data could be the duration of the pulses within the output signal 125 of the control circuitry 123. In some examples the data could be estimates of the time constants $T_1$ and $T_2$ which may have been obtained by processing the output signal 125 of the control circuitry 123.

The data may be stored in processed or unprocessed format remotely at one or more devices. The data may be stored in the Cloud.

The data may be processed remotely at one or more devices. The data may be partially processed locally and partially processed remotely at one or more devices.

The data may be communicated to the remote devices wirelessly via short range radio communications such as Wi-Fi or Bluetooth, for example, or over long range cellular radio links. In some examples the data may be communicated via a human body communication (HBC) system or other suitable system. The apparatus may comprise a communications interface such as, for example, a radio transceiver for communication of data.

The electronic device 401 may be part of the Internet of Things forming part of a larger, distributed network.

The processing of the data, whether local or remote, may be for the purpose of health monitoring, data aggregation, patient monitoring, vital signs monitoring or other purposes.

The processing of the data, whether local or remote, may produce an output. The output may be communicated to the electronic device 401 where it may produce an output sensible to the subject 105 such as an audio output, visual output or haptic output.

Figure 5:
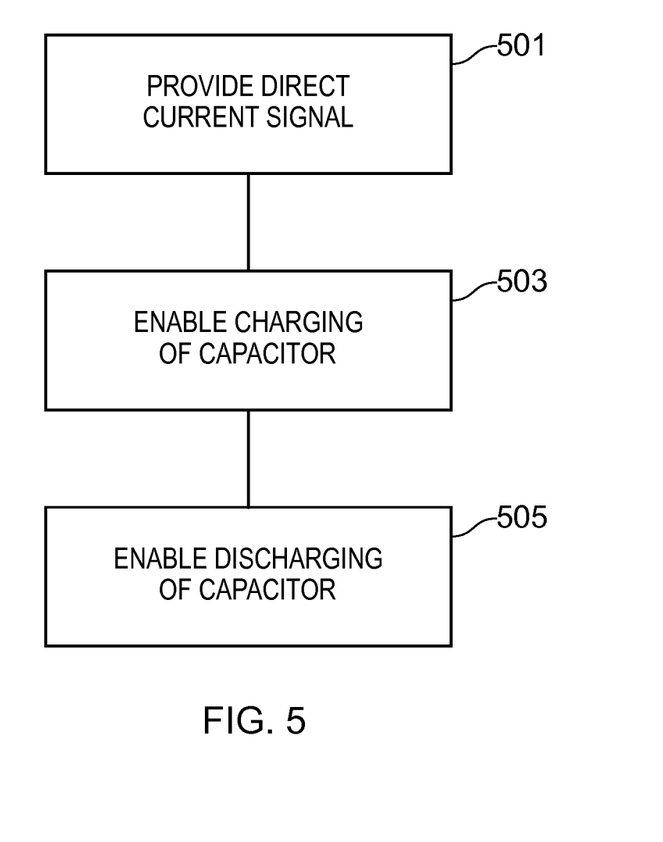
FIG. 5 shows an example embodiment of a method.

FIG. 5 shows an example embodiment of a method. The method may be implemented using apparatus 101 and/or electronic devices as described above.

The method comprises, at block 501, configuring circuitry 103 to provide a direct current signal to a subject 105. At block 503 the method comprises configuring the circuitry 103 to enable charging of a capacitor 111 through a first current loop 107. The charging of the capacitor 111 enables measurement of a first time constant $T_1$ to be obtained where the first time constant $T_1$ is indicative of a charging time of the capacitor 111.

The method also comprises, at block 505, configuring the circuitry 103 to enable discharging of the capacitor 111 through a second current loop 109. The discharging of the capacitor 111 enables measurement of a second time constant $T_2$ to be obtained where the second time constant $T_2$ is indicative of a discharging time of the capacitor 111.

The first time constant $T_1$ and the second time constant $T_2$ enable an impedance of the subject 105 to be estimated. The impedance of the subject 105 could be estimated by processing circuitry. The impedance of the subject 105 could be estimated by using lookup tables or any other suitable means.

Examples of the disclosure provide for an apparatus 101, electronic device 401 and method which enable the impedance of the subject 105 to be determined using a direct current signal. This may reduce the power requirements of the apparatus 101 and may reduce the complexity of the circuitry 103 needed compared to an apparatus 101 using an alternating current signal.

Also as a low power signal is used this may enable the apparatus 101 to be used for extended periods of time. This may enable the apparatus 101 to be used in a wearable electronic device 401. This may enable the apparatus 101 to be used to monitor the impedance of the subject 105 over extended periods of time.

In this description the term coupled means operationally coupled. Any number or combination of intervening elements can exist between coupled components including no intervening elements.

The above described examples find application as enabling components of: automotive systems; telecommunication systems; electronic systems including consumer electronic products; distributed computing systems; media systems for generating or rendering media content including audio, visual and audio visual content and mixed, mediated, virtual and/or augmented reality; personal systems including personal health systems or personal fitness systems; navigation systems; user interfaces also known as human machine interfaces; networks including cellular, non-cellular, and optical networks; ad-hoc networks; the internet; the internet of things; virtualized networks; and related software and services.

The term "comprise" is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term "example" or "for example" or "can" or "may" in the text denotes, whether explicitly stated or not, that such features or functions are present in at least the described example, whether described as an example or not, and that they can be, but are not necessarily, present in some of or all other examples. Thus "example", "for example", 'can' or '"may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although embodiments have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain embodiments, those features may also be present in other embodiments whether described or not.

The term "a" or "the" is used in this document with an inclusive not an exclusive meaning. That is any reference to X comprising a/the Y indicates that X may comprise only one Y or may comprise more than one Y unless the context clearly indicates the contrary. If it is intended to use "a" or "the" with an exclusive meaning then it will be made clear in the context. In some circumstances the use of "at least one'" or "one or more" may be used to emphasis an inclusive meaning but the absence of these terms should not be taken to infer and exclusive meaning.

The presence of a feature (or combination of features) in a claim is a reference to that feature) or combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

The use of the term "'example" or "for example" or "can" or "may" in the text denotes, whether explicitly stated or not, that such features or functions are present in at least the described example, whether described as an example or not, and that they can be, but are not necessarily, present in some of or all other examples. Thus "example", "for example", "can" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:
1. An apparatus comprising:
circuitry configured to provide a direct current signal to a subject;
wherein the circuitry comprises a capacitor and the circuitry is configured to enable switching between a first circuit loop and a second circuit loop, the first circuit loop comprising the capacitor that is in series with the subject when the apparatus is in use and the circuitry is coupled to the subject, and the second circuit loop comprising the capacitor that is in series with the subject when the apparatus is in use and the circuitry is coupled to the subject, and wherein the first circuit loop is configured to enable charging of the capacitor using the direct current signal to enable measurement of a first time constant to be obtained where the first time constant is indicative of a charging time of the capacitor and the second circuit loop is configured to enable discharging of the capacitor to enable measurement of a second time constant to be obtained where the second time constant is indicative of a discharging time of the capacitor; and
wherein the first time constant and the second time constant enable an impedance of the subject to be estimated.

2. An apparatus as claimed in claim 1 wherein the circuitry is configured to provide an output signal comprising information indicative of the first time constant and the second time constant.

3. An apparatus as claimed in claim 1 wherein the first circuit loop comprises a power source that produces the direct current signal.

4. An apparatus as claimed in claim 1 wherein the first circuit loop comprises a first resistor and the second circuit loop comprises a second resistor.

5. An apparatus as claimed in claim 4 wherein the first resistor has a different resistance to the second resistor.

6. An apparatus as claimed in claim 4 wherein the first resistor is connected in series with the capacitor when the first circuit loop has been switched to, and wherein the second resistor is connected in series with the capacitor when the second circuit loop has been switched to.

7. An apparatus as claimed claim 4 comprising compensation circuitry configured to detect a change in impedance at an interface between the circuitry and the subject and, in response to the detected change, adjust the resistance of the first resistor and/or the second resistor.

8. An apparatus as claimed in claim 1 comprising-one or more switches configured to close the first circuit loop and open the second circuit loop for a first time period and close the second circuit loop and open the first circuit loop for-the-a second time period wherein the first time period is different to the second time period.

9. An apparatus as claimed in claim 8 comprising control circuitry configured to cause a first switch to be opened and a second switch to be closed in response to a threshold voltage level being reached, wherein when the first switch is opened and the second switch is closed, the circuitry switches to the second circuit loop.

10. An apparatus as claimed in claim 9 wherein the control circuitry is configured to provide output pulses wherein duration of the output pulses provides an indication of the first time constant and/or the second time constant.

11. An apparatus as claimed in claim 10 comprising processing circuitry configured to estimate an impedance of the subject from the output pulses of the control circuitry.

12. An apparatus as claimed in claim 9 wherein the control circuitry comprises at least one of a Schmitt trigger, a window comparator, which is configured to control positions of the switches based on a threshold voltage being reached.

13. An apparatus as claimed in claim 12 wherein-the-impedance of the subject is estimated using look up tables.

14. An apparatus as claimed in claim 1 comprising at least a first electrode and at least a second electrode that are configured to provide an interface between the circuitry and the subject and to couple the circuitry to the subject.

15. An apparatus as claimed in claim 1 wherein:
the circuitry is configured to disconnect the first circuit loop from the capacitor when the second circuit loop is used, the apparatus is in use, and the circuitry is coupled to the subject; and
the circuitry is configured to disconnect the second circuit loop from the capacitor when the first circuit loop is used, the apparatus is in use, and the circuitry is coupled to the subject.

16. A method comprising:
configuring an apparatus comprising circuitry, comprising a capacitor, to provide a direct current signal to a subject;
configuring the circuitry to switch to a first circuit loop to enable charging of the capacitor using the direct current signal through the first circuit loop comprising the capacitor that is in series with the subject when the apparatus is in use and the circuitry is coupled to the subject so as to enable measurement of a first time constant to be obtained where the first time constant is indicative of a charging time of the capacitor; and
configuring the circuitry to switch to a second circuit loop to enable discharging of the capacitor through the second circuit loop comprising the capacitor that is in series with the subject when the apparatus is in use and the circuitry is coupled to the subject so as to enable measurement of a second time constant to be obtained where the second time constant is indicative of a discharging time of the capacitor,
wherein the first time constant and the second time constant enable an impedance of the subject to be estimated.

17. A method as claimed in claim 16 comprising configuring the circuitry to provide an output signal comprising information indicative of the first time constant and the second time constant.

18. A method as claimed in claim 16 wherein the first circuit loop comprises a first resistor and the second circuit loop comprises a second resistor.

19. A method as claimed in claim 18 wherein the first resistor has a different resistance to the second resistor.

\* \* \* \* \*